United States Patent
Bare et al.

(10) Patent No.: US 11,617,784 B2
(45) Date of Patent: *Apr. 4, 2023

(54) SYSTEMS AND METHODS FOR PREPARING A THROMBIN SERUM

(71) Applicant: ARTHREX, INC., Naples, FL (US)

(72) Inventors: Christopher Bare, Naples, FL (US); Abigail Nabors, Naples, FL (US); Melissa Tucker, Bonita Springs, FL (US); Robert Harrison, Naples, FL (US)

(73) Assignee: ARTHREX, INC., Naples, FL (US)

( * ) Notice: Subject to any disclaimer, the term of this patent is extended or adjusted under 35 U.S.C. 154(b) by 162 days.

This patent is subject to a terminal disclaimer.

(21) Appl. No.: 17/325,358

(22) Filed: May 20, 2021

(65) Prior Publication Data

US 2021/0268077 A1  Sep. 2, 2021

Related U.S. Application Data

(60) Continuation of application No. 16/812,592, filed on Mar. 9, 2020, now Pat. No. 11,045,526, which is a
(Continued)

(51) Int. Cl.
  *A61K 38/48* (2006.01)
  *B01L 3/00* (2006.01)
  *C12N 9/74* (2006.01)

(52) U.S. Cl.
  CPC ........ *A61K 38/4833* (2013.01); *B01L 3/5021* (2013.01); *B01L 3/50825* (2013.01);
(Continued)

(58) Field of Classification Search
  CPC ............... A61K 38/4833; B01L 3/5021; B01L 3/50825; B01L 2200/026; B01L 2300/026;
(Continued)

(56) References Cited

U.S. PATENT DOCUMENTS 4,257,886 A  3/1981  Kessler
4,904,601 A  2/1990  Mano et al.
(Continued)

FOREIGN PATENT DOCUMENTS

CA  1040170 A  10/1978
EP  2687217 A1  1/2014
(Continued)

OTHER PUBLICATIONS

Biomet, Clotalyst® autologous Activation Solution, 2012 Biomet Orthopedics, Form No. BMET0248.0, REV121512.
(Continued)

*Primary Examiner* — Michael L Hobbs
(74) *Attorney, Agent, or Firm* — DLA Piper LLP US

(57) ABSTRACT

A system for preparing a thrombin serum that can include a containment device, a cage received within the containment device, a cap attachable to the containment device, an inlet port configured to introduce a non-anti-coagulated autologous blood fluid into the containment device, and an outlet port. An activator, such as glass beads, can be present within the containment device.

15 Claims, 8 Drawing Sheets

Related U.S. Application Data division of application No. 15/455,417, filed on Mar. 10, 2017, now Pat. No. 10,596,236.

(60) Provisional application No. 62/306,304, filed on Mar. 10, 2016.

(52) U.S. Cl.
CPC .... *C12N 9/6429* (2013.01); *C12Y 304/21005* (2013.01); *B01L 2200/026* (2013.01); *B01L 2300/026* (2013.01); *B01L 2300/041* (2013.01); *B01L 2300/042* (2013.01); *B01L 2300/047* (2013.01); *B01L 2300/0609* (2013.01); *B01L 2300/0681* (2013.01); *B01L 2300/0832* (2013.01); *B01L 2300/16* (2013.01)

(58) Field of Classification Search
CPC ......... B01L 2300/041; B01L 2300/042; B01L 2300/047; B01L 2300/0609; B01L 2300/0681; B01L 2300/0832; B01L 2300/16; C12N 9/6429; C12Y 304/21005
See application file for complete search history.

(56) References Cited

U.S. PATENT DOCUMENTS

| | | | |
|---|---|---|---|
| 5,126,269 | A | 6/1992 | Fike et al. |
| 5,776,336 | A | 7/1998 | Holm |
| 5,998,184 | A | 12/1999 | Shi |
| 6,099,493 | A | 8/2000 | Swisher |
| 6,416,717 | B1 | 7/2002 | Suzuki |
| 6,503,731 | B2 | 1/2003 | Marx |
| 6,558,341 | B1 | 5/2003 | Swisher |
| 6,713,246 | B1 | 3/2004 | Reinecke |
| 6,719,901 | B2 | 4/2004 | Dolecek |
| 6,905,612 | B2 | 6/2005 | Dorian |
| 7,025,212 | B2 | 4/2006 | Amano |
| 7,553,413 | B2 | 6/2009 | Dorian |
| 8,177,072 | B2 | 5/2012 | Chapman et al. |
| 8,187,475 | B2 | 5/2012 | Hecker et al. |
| 8,419,705 | B2 | 4/2013 | Omori |
| 8,460,227 | B2 | 6/2013 | Bare et al. |
| 8,506,823 | B2 | 8/2013 | Chapman et al. |
| 8,511,479 | B2 | 8/2013 | Chapman et al. |
| 8,511,480 | B2 | 8/2013 | Chapman et al. |
| 8,586,324 | B2 | 11/2013 | Leach et al. |
| 8,603,345 | B2 | 12/2013 | Ross |
| 8,753,690 | B2 | 6/2014 | Higgins et al. |
| 8,783,470 | B2 | 7/2014 | Hecker et al. |
| 8,796,017 | B2 | 8/2014 | Suzuki |
| 9,011,687 | B2 | 4/2015 | Swift |
| 9,011,846 | B2 | 4/2015 | Overholser et al. |
| 9,119,829 | B2 | 9/2015 | Higgins |
| 9,205,110 | B2 | 12/2015 | Bare |
| 9,480,730 | B2 | 11/2016 | Chapman |
| 9,629,798 | B2 | 4/2017 | Senderoff |
| 9,815,038 | B2 | 11/2017 | Leach |
| 11,045,526 | B2 * | 6/2021 | Bare ................... A61K 38/4833 |
| 2001/0015338 | A1 | 8/2001 | Nanba |
| 2002/0065047 | A1 | 5/2002 | Moose |
| 2003/0010718 | A1 | 1/2003 | Burbank |
| 2004/0120942 | A1 | 6/2004 | McGinnis et al. |
| 2005/0271646 | A1 | 12/2005 | Delmotte |
| 2006/0134094 | A2 | 6/2006 | Delmotte |
| 2006/0278588 | A1 | 12/2006 | Woodnell-May |
| 2008/0020049 | A1 | 1/2008 | Darling |
| 2008/0047908 | A1 | 2/2008 | Sekine |
| 2008/0220462 | A1 | 9/2008 | Bell |
| 2008/0267940 | A1 | 10/2008 | Mohammed |
| 2008/0274496 | A1 | 11/2008 | Duymelinck et al. |
| 2009/0105611 | A1 * | 4/2009 | Wilkinson ............... G01N 1/36 600/577 |
| 2009/0148941 | A1 | 6/2009 | Florez et al. |
| 2009/0152744 | A1 | 6/2009 | Mou |
| 2011/0183406 | A1 | 7/2011 | Kensey |
| 2012/0115181 | A1 | 5/2012 | Al-Rasheed |
| 2013/0178425 | A1 | 7/2013 | Higgins |
| 2014/0249071 | A1 | 9/2014 | Bare |
| 2014/0271870 | A1 * | 9/2014 | O'Shaughnessey ... A61K 38/19 514/7.6 |
| 2014/0274895 | A1 | 9/2014 | Binder |
| 2014/0319081 | A1 | 10/2014 | Davey |
| 2015/0182202 | A1 | 7/2015 | Wan |
| 2015/0182603 | A1 | 7/2015 | Chapman |
| 2016/0106117 | A1 | 4/2016 | Gazenko |
| 2017/0027822 | A1 | 2/2017 | Margolin et al. |
| 2017/0087228 | A1 | 3/2017 | Turzi |
| 2017/0189537 | A1 | 7/2017 | Senderoff |
| 2017/0258877 | A1 | 9/2017 | Bare |
| 2017/0336424 | A1 | 11/2017 | Rida |
| 2017/0361317 | A1 | 12/2017 | Wilkinson |
| 2018/0015147 | A1 | 1/2018 | Bouckenooghe |
| 2018/0110917 | A1 | 4/2018 | Turzi |

FOREIGN PATENT DOCUMENTS

| | | |
|---|---|---|
| GB | 2433219 A | 6/2007 |
| WO | 2007014742 A1 | 2/2007 |
| WO | 20140149301 A1 | 9/2014 |
| WO | 20170156375 A1 | 9/2017 |

OTHER PUBLICATIONS

BioPharm Laboratories Preparation of Serum from Anticoagulated Blood, Jun. 20, 2012, retrieved from the internet: http://www.biopharmalaboratories.com/files/4296292/uploaded/080812-Preparation%of%20Serum%20from%20Plasma.pdf.

International Preliminary Report on Patentability for Application No. PCT/US2017/021757, dated Sep. 20, 2018.

International Preliminary Report on Patentability for corresponding PCT application No. PCT/US2017/021757, dated Sep. 11, 2018.

International Search Report and Written Opinion of the International Searching Authority for International Application No. PCT/US2017/021751, dated Aug. 4, 2017.

International Search Reporton Patentability for corresponding PCT application No. PCT/US2017/021757, dated Jul. 19, 2018.

The Partial International Search for International Application No. PCT/US2017/021751, dated Jun. 14, 2017.

U.S. Appl. No. 15/455,474, Final Office Action dated Nov. 19, 2019, 13 pages.

U.S. Appl. No. 15/455,474, Office Action dated Oct. 11, 2019, 8 pages.

* cited by examiner

# SYSTEMS AND METHODS FOR PREPARING A THROMBIN SERUM

CROSS-REFERENCE TO RELATED APPLICATIONS

This application is a continuation of U.S. application Ser. No. 16/812,592, filed Mar. 9, 2020, now U.S. Pat. No. 11,045,526, which is a divisional of U.S. application Ser. No. 15/455,417, filed on Mar. 10, 2017, now U.S. Pat. No. 10,596,236, issued Mar. 24, 2020, which claims the benefit of U.S. Provisional Application No. 62/306,304, filed on Mar. 10, 2016, the entirety of which are incorporated herein by reference.

BACKGROUND

This disclosure relates to systems and methods for preparing a thrombin serum.

Thrombin is an enzyme in blood plasma that clots blood by converting fibrinogen to fibrin. Thrombin has many surgical uses and can be used to treat wounds or control bleeding during surgical procedures.

SUMMARY

This disclosure describes systems and methods for preparing a thrombin serum. The thrombin serum can be used to produce a clotted product.

An exemplary system for preparing a thrombin serum includes a containment device and an activator (e.g., a plurality of beads or spheres) to artificially start the coagulation cascade after adding an autologous blood fluid to the containment device. The system can produce a thrombin serum from a non-anticoagulated autologous blood fluid. Once prepared, the thrombin serum can be added to platelet rich plasma or other autologous blood fluids to produce a clot.

A system for preparing a thrombin serum according to an exemplary aspect of the present disclosure includes, inter alia, a containment device, a cage received within the containment device, a cap attached to the containment device, an inlet port configured to introduce a non-anticoagulated autologous blood fluid into the containment device, and an outlet port configured to remove a thrombin serum from the containment device.

A method for preparing a thrombin serum according to another exemplary aspect of the present disclosure includes, inter alia, adding a first amount of a non-anti-coagulated autologous blood fluid to a containment device, incubating the containment device, extracting a thrombin serum from containment device, and adding the thrombin serum to a second autologous blood fluid to produce a clotted product.

DETAILED DESCRIPTION

This disclosure describes systems and methods for preparing a thrombin serum. Once prepared, thrombin serum can be used to produce a clot in an autologous blood fluid such as platelet rich plasma (PRP). The clotted product is then used at the point of care to treat a patient.

In some embodiments, a system for preparing the thrombin serum includes a containment device and an activator, such as a plurality of beads, received within the containment device. An activator such as glass beads can artificially start the coagulation cascade when autologous blood fluid is added to the containment device. A thrombin serum can be produced via the methods described herein, which include contacting an activator with an autologous blood fluid (e.g., whole blood, platelet-rich plasma (PRP), platelet-poor plasma (PPP), bone marrow aspirate (BMA), bone marrow concentrate (BMC), or combinations thereof). The thrombin serum may be extracted from the containment device and then added to a second autologous blood fluid to produce a clot. These and other features are discussed in greater detail in the following paragraphs of this detailed description.

Figure 1:
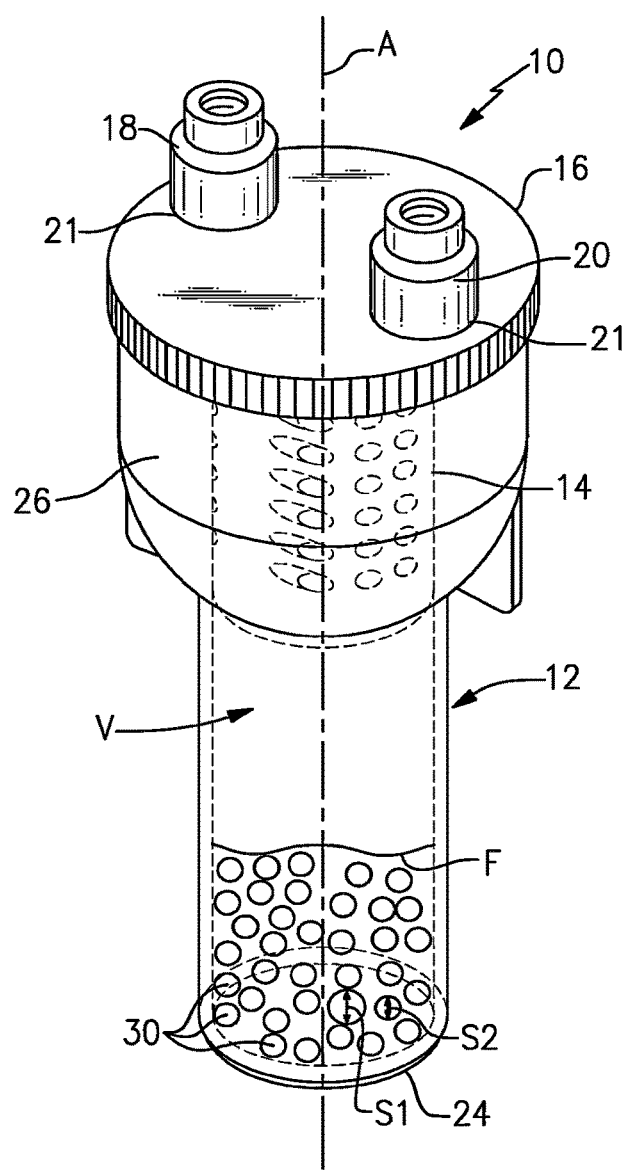
FIG. 1 illustrates a system for preparing a thrombin serum.
Figure 2:
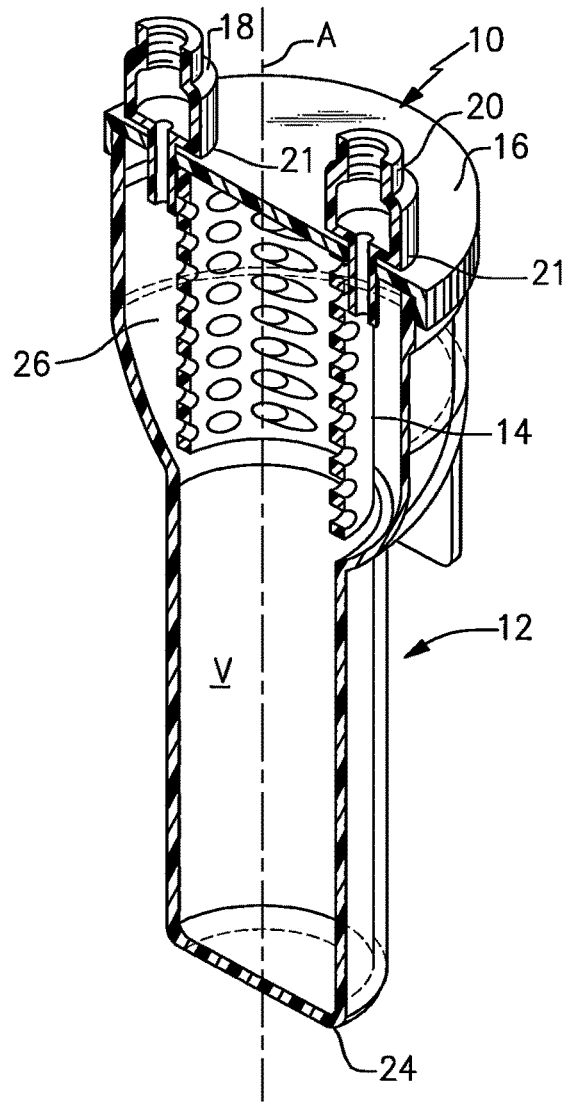
FIG. 2 illustrates a cross-sectional view of the system of FIG. 1.

FIGS. 1 and 2 illustrate a system 10 for preparing a thrombin serum. Thrombin is an enzyme in blood plasma that clots blood by converting fibrinogen to fibrin. A thrombin serum is a blood serum comprising thrombin at greater than basal levels. The thrombin serums of this disclosure may therefore be used in a wide variety of surgical procedures, including but not limited to controlling bleeding, treating wounds, augmenting tissue repairs, repairing/plugging voids in tissue or bone, etc.

In an embodiment, a method of preparing a thrombin serum includes contacting an autologous blood fluid with an activator. Following contact, the autologous blood fluid is incubated with the activator in a containment device to produce a thrombin serum. The incubation may occur at room temperature. The autologous blood fluid may include whole blood, PRP, PPP, BMA, BMC, or combinations thereof, for example. In an embodiment, an autologous blood fluid contacts and is incubated with an activator without any other substance present. In an embodiment, different autologous blood fluids are used during the contacting and incubating steps of a method for preparing a thrombin serum. In an embodiment, a containment device can be a containment device as described herein.

In an embodiment, a method of preparing a thrombin serum can include multiple incubations and agitations. Following initial contact, the autologous blood fluid and an activator can be mixed (e.g., inversion of the containment device, inverting the containment device 5 to 10 times), and in an embodiment, gently mixed. Following mixture, the autologous blood fluid and the activator can be incubated. In an embodiment, the incubation can be about 5 to about 15 minutes, about 5 to about 10 minutes, about 5 to about 9 minutes, about 5 to about 8 minutes, about 5 to about 7 minutes, about 5 to about 6 minutes, about 6 to about 15 minutes, about 6 to about 10 minutes, about 6 to about 9 minutes, about 6 to about 8 minutes, or about 6 to about 7 minutes. In an embodiment, an autologous blood fluid and an activator can be incubated for about 5, about 6, about 7, about 8, about 9, about 10, about 11, about 12, about 13, about 14, or about 15 minutes following mixture.

Following the first incubation, an additional blood product can optionally be added to the autologous blood product and activator. If the autologous blood product includes an anticoagulant, then CaC12 is added following the first incubation. The mixture is then vigorously mixed (e.g., vortexing, shaking, sharp inversion, etc.). If no additional blood product or CaC12 is added, the combination of autologous blood product and activator is vigorously mixed as well. Following the vigorous mixing, the mixture is incubated for about 1, about 2, about 3, about 4, or about 5 minutes. The mixture can then be vigorously mixed again for about 3 to 15 minutes, about 3 to 10 minutes, about 5 to 10 minutes, or about 5 to 15 minutes. In an embodiment, an incubation is about 3, about 4, about 5, about 6, about 7, about 8, about 9, about 10, about 11, about 12, about 13, about 14, or about 15 minutes. The mixture can be incubated until at least a clot begins to form. Following a last incubation, thrombin serum is withdrawn from the containment device.

In an embodiment of the method to prepare a thrombin serum, all steps are performed at room temperature.

The exemplary system 10 may include a containment device 12, a cage 14, a cap 16, an inlet port 18 and an outlet port 20. In a non-limiting embodiment, the containment device 12 is configured as a test tube. However, containment devices having other sizes, shapes and configurations are also contemplated within the scope of this disclosure. In another non-limiting embodiment, the containment device 12 is made of a sterilizable material, such as any suitable glass, ceramic or plastic material. In yet another non-limiting embodiment, the containment device 12 is made of a transparent material for visualizing the contents of the containment device 12 during its use.

The containment device 12 extends along a longitudinal axis A between a proximal opening 22 and a closed distal end 24. An internal volume V of the containment device 12 is configured to hold an activator. In an embodiment, an activator can be a plurality of beads 30 (see FIG. 1). In a non-limiting embodiment, the beads 30 are borosilicate beads, metal beads, or plastic beads; however, the beads 30 may be manufactured from any glass like composition including but not limited to alumina, silicate, quartz, bioglass, ceramic glass, flint glass, fluorosilicate glass, phosphosilicate glass, cobalt glass or conundrum. The beads 30 may also be spherical shaped to provide for maximum surface area contact with an autologous blood fluid F that can also be added to the internal volume V of the containment device 12.

The beads 30 are optionally coated to maximize interaction with the autologous blood fluid F. The coating could be a hydrophilic or hydrophobic surface coating and could include silane, surfactants, polyether, polyester, polyurethane, or polyol groups, for example. The coating may optionally be applied to one or more of the beads 30, the cage 14, and an inner surface of the containment device 12.

In another non-limiting embodiment, the beads 30 include a first amount of beads having a first size Si and a second amount of beads having a second size S2 that is larger than the first size S1. For example, in a further non-limiting embodiment, the containment device 12 holds approximately 1.5 g of 200 um borosilicate beads and approximately 2500 mg of 3 mm borosilicate beads. However, other bead amounts and bead sizes are contemplated within the scope of this disclosure, and the specific bead characteristics may be tailored to match the amount of desired interaction between the beads 30 and the autologous blood fluid F received inside the containment device 12.

The cap 16 may be either fixedly or removably attachable to the containment device 12 to cover the proximal opening 22 and selectively conceal the contents of the containment device 12. In a non-limiting embodiment, the cap 16 is threadably attached to the containment device 12. In another non-limiting embodiment, the cap 16 is press-fit onto the containment device 12. Other containment device-to-cap connections are also contemplated within the scope of this disclosure.

The inlet port 18 and the outlet port 20 are received through openings 21 formed in the cap 16. In a non-limiting embodiment, the inlet port 18 and the outlet port 20 are luer-type connectors adapted for lockingly engaging a tip of a syringe (syringe not shown in FIGS. 1 and 2). The inlet port 18 may be used to deliver autologous blood fluids F into the internal volume V of the containment device 12. The outlet port 20 may be used to remove a thrombin serum from the containment device 12 after the autologous blood fluid F has been exposed to and has interacted with the beads 30 to produce thrombin. The thrombin serum can then be retrieved through the outlet port 20 for subsequent use to create in a clot. The inlet port 18 and the outlet port 20 are swabbable valves, in another non-limiting embodiment.

Figure 3:
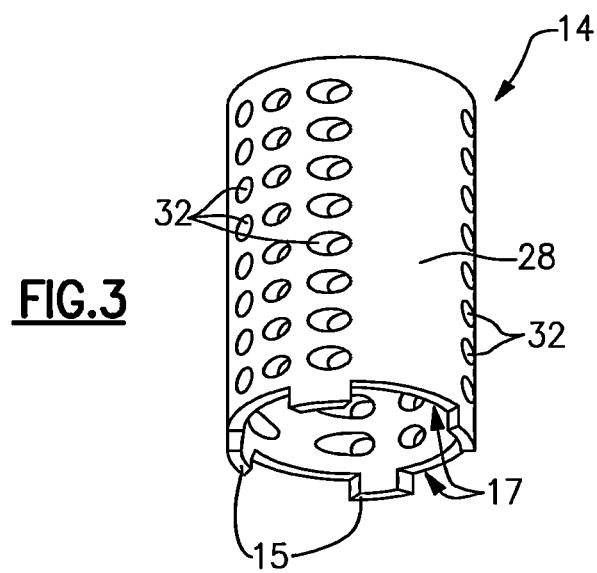
FIG. 3 illustrates a cage of the system of FIG. 1.

Referring now to FIGS. 1-3, the cage 14 is positioned inside the containment device 12. Among other functions, the cage 14 prevents clogging of the inlet port 18 and the outlet port 20. In other words, the cage 14 can act as a filter to prevent clogging. In a non-limiting embodiment, the cage 14 is positioned within a flared portion 26 of the containment device 12. The flared portion 26 is proximate to the proximal opening 22. The cage 14 may be either securely affixed (e.g., welded, etc.) inside the containment device 12 or removable from the containment device 12. The cage 14 may include legs 15 that aid to position and/or secure the cage 14 inside the containment device 12. Slots 17 extend between the legs 15. The cage 14 can include any number of legs 15 and slots 17.

The cage 14 may further include a cylindrical body 28, although other shapes are also contemplated within the scope of this disclosure. In a first non-limiting embodiment, the cylindrical body 28 is a hollow cylinder that includes an open top and open bottom (see FIG. 4). Thus, in some embodiments, the cage 14 is a floorless structure. A plurality of openings 32 may extend through the cylindrical body 28 of the cage 14. Once introduced into the containment device 12, the autologous blood fluid F may pass through the openings 32 and be exposed to the beads 30 that have already been positioned inside the containment device 12. Exposure to the beads 30 artificially starts the coagulation cascade within the autologous blood fluid F. The cells of the autologous blood fluid F thus release thrombin which can be harvested from the autologous blood fluid F and used to produce a clot, as is further described below.

Figure 4:
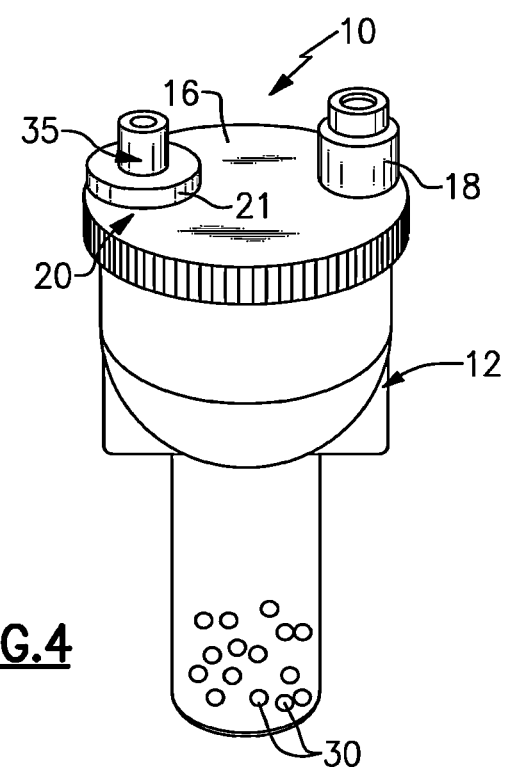
FIG. 4 illustrates a filter of the system of FIG. 1.

Referring to FIG. 4, a filter 35 may optionally attach to either the outlet port 20 or the opening 21 that receives the outlet port 20. The filter 35 can connect to either the outlet port 20 or the opening 21 via a luer-lock connection, for example. In a further non-limiting embodiment, the filter 35 is a macro-filter that substantially prevents the beads 30 from clogging the outlet port 20 during extraction of the thrombin serum.

Figure 5A:
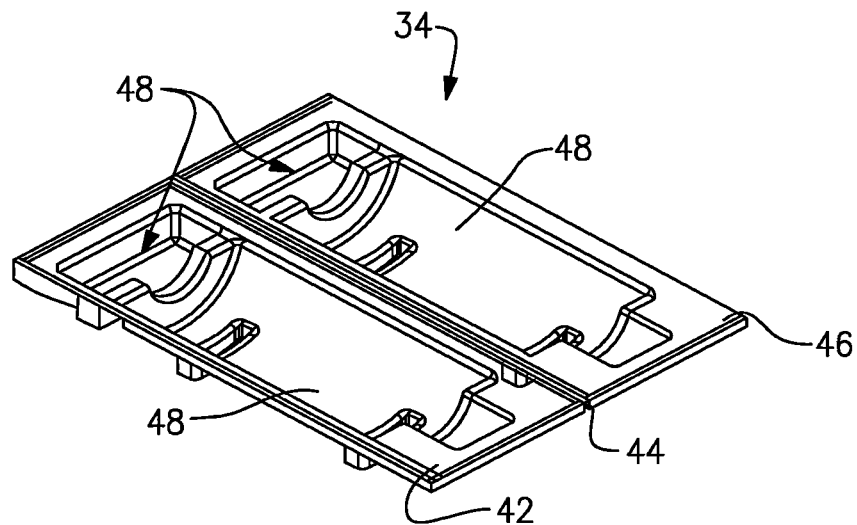
FIGS. 5A and 5B illustrate a tray assembly for packaging a system for preparing a thrombin serum.
Figure 5B:
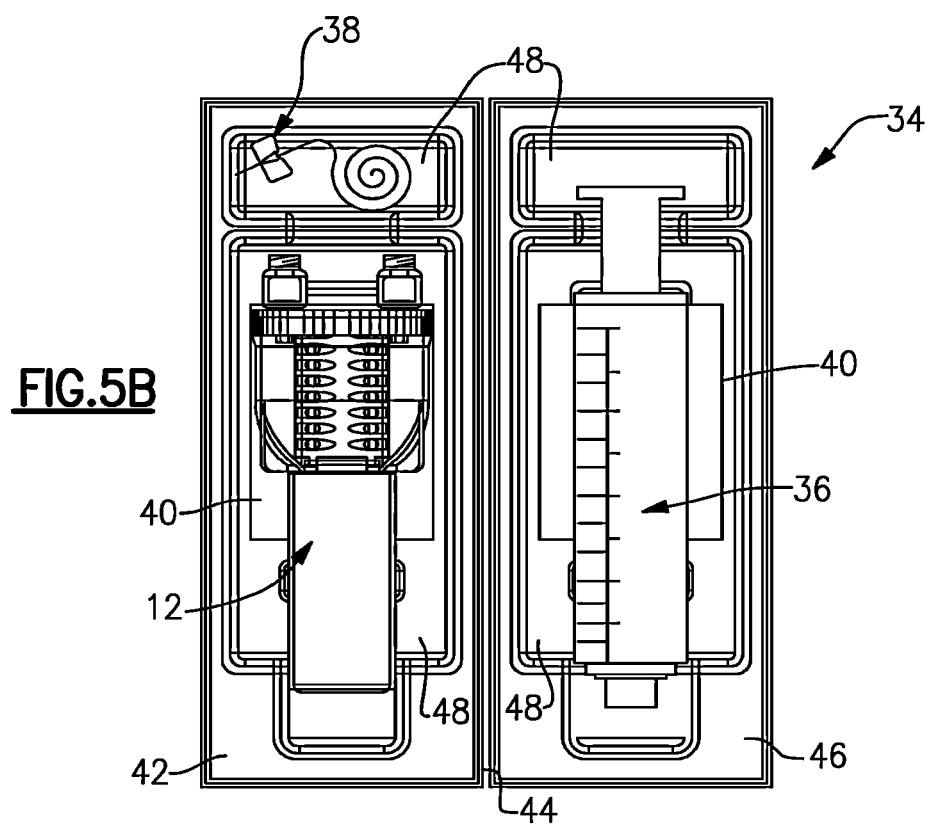

FIGS. 5A and 5B illustrate an optional tray assembly 34 for conveniently packaging the various components of the system 10. For example, the tray assembly 34 may package the containment device 12, a syringe 36, a needle 38, and hand warmers 40 of the system 10. In a first non-limiting embodiment, the tray assembly 34 includes a first housing 42 that is connected to a second housing 46 along a hinge 44. The first housing 42 is foldable about the hinge 44 to a position over top of the second housing 46 to enclose the system 10. In another non-limiting embodiment, the first housing 42 is separate from and connectable to the second housing 46, such as by using a snap-fit or interference connection. Each housing 42, 46 includes one or more receptacles 48 for receiving one or more of the containment device 12, the syringe 36, the needle 38, the hand warmers 40 and/or any other component of the system 10. The first and second housings 42, 46 may be made of an insulating material.

In another non-limiting embodiment, the tray assembly 34 is employable as a portable incubator. For example, after adding the beads 30 and the autologous blood fluid F to the containment device 12, the hand warmers 40 are activated in a known manner and the containment device 12 is placed inside the tray assembly 34 along with the activated hand warmers 40. In a non-limiting embodiment, each hand warmer 40 is positioned within one of the receptacles 48 such that it is between the tray assembly 34 and the containment device 12. The tray assembly 34 is then concealed by connecting the first housing 42 to the second housing 46. The hand warmers 40 release heat that augments interaction/incubation between the autologous blood fluid F and the beads 30, thus promoting the production of a thrombin serum. The thrombin serum can be extracted from the containment device 12 using the syringe 36 and can subsequently be used to produce a clot.

FIGS. 6 through 13B, with continued reference to FIGS. 1-5B, schematically illustrate an exemplary surgical technique for preparing a thrombin serum and utilizing the thrombin serum to produce a clot. These figures illustrate, in sequential order, a non-limiting embodiment for preparing a thrombin serum that can be used to produce a clot in an autologous blood fluid. It should be understood; however, that fewer or additional steps than are recited below could be performed and that the recited order of steps is not intended to limit this disclosure.

Figure 6:
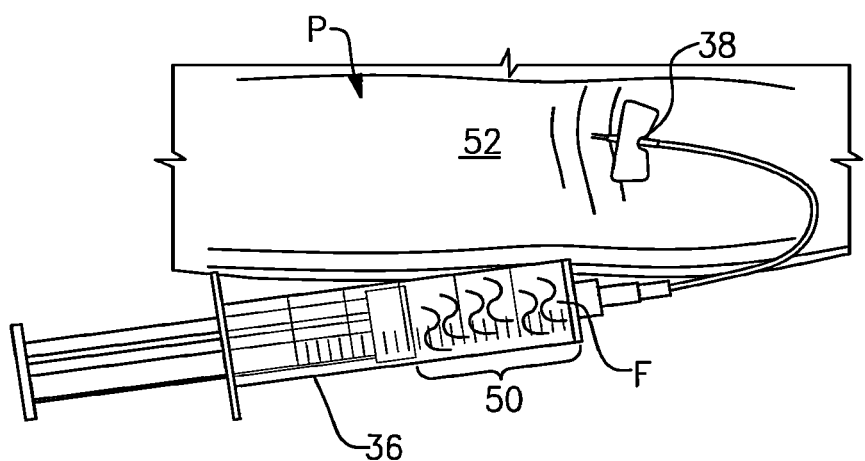
FIG. 6 schematically illustrates harvesting an autologous blood fluid sample from a patient.

Referring first to FIG. 6, a sample 50 of an autologous blood fluid F may be harvested from a body 52 of a patient P. The sample 50 may be harvested from veinous whole blood of the patient P or from a bone of the Patient P. In a non-limiting embodiment, the sample 50 is collected using the syringe 36 and the needle 38 of the system 10.

The sample 50 can be used to prepare a blood-derived autologous blood fluid F, such as PRP, PPP, or a combination of these fluids. For example, the autologous blood fluid F may be prepared having a concentrated platelet formulation. Various preparation techniques may optionally be performed on the sample 50 to prepare an autologous blood fluid F having a customized platelet formulation. By way of two non-limiting examples, the autologous blood fluid F could optionally be prepared using the Arthrex Angel System™ or the Arthrex ACP® System, both available from Arthrex, Inc.

Figure 7:
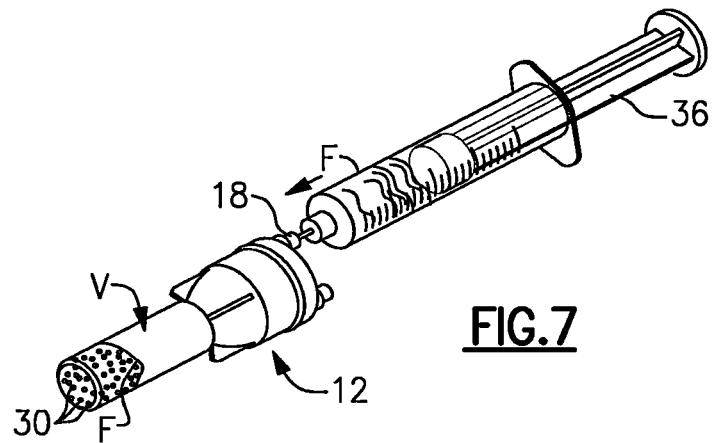
FIG. 7 illustrates adding an autologous blood fluid to a containment device of a system for preparing a thrombin serum.

Referring now to FIG. 7, an autologous blood fluid F is introduced into the containment device 12. The autologous blood fluid F may include whole blood, PRP, PPP, or any combinations of these fluids. In a non-limiting embodiment, the autologous blood fluid F that is added to the containment device 12 is a non-anti-coagulated autologous blood fluid in that it does not contain any anticoagulants such as Acid Citrate Dextrose Solution A (ACDA). Alternatively, if an autologous blood fluid F having an anticoagulant is used, calcium chloride may be added to the autologous blood fluid F to overcome the effects of the anticoagulant.

In either case, the autologous blood fluid F may be introduced into the containment device 12 by connecting the syringe 36 to the inlet port 18 and then injecting the conditioned autologous blood fluid F into the internal volume V of the containment device 12. The beads 30 and the autologous blood fluid F are exposed to one another inside the containment device 12. This exposure artificially starts the coagulation cascade and therefore causes the cells within the autologous blood fluid F to begin to produce thrombin.

Figure 8:
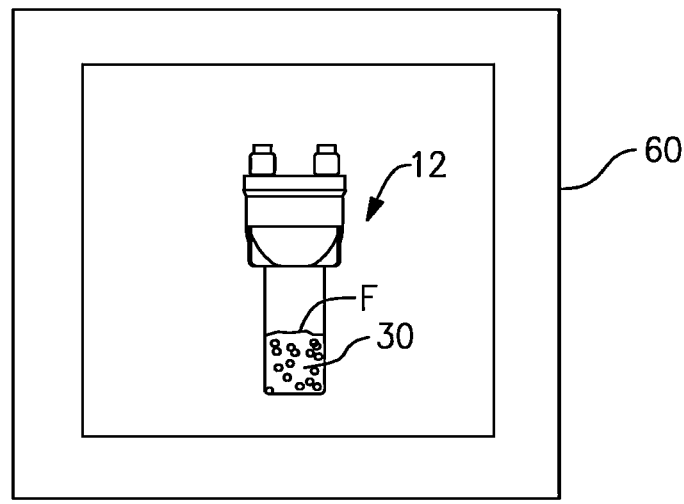
FIG. 8 schematically illustrates incubating the containment device.

The containment device 12 may next be gently inverted and then incubated for approximately six to twenty minutes. In a first non-limiting embodiment, the containment device 12 is incubated until a gel is formed, which may occur after approximately seven minutes or longer at ambient conditions. The containment device 12 may be incubated on a table top at room temperature. In another non-limiting embodiment, the containment device 12 is incubated within an incubation device 60 as schematically shown in FIG. 8. The incubation device 60 could be any known incubator. In yet another non-limiting embodiment, the incubation device 60 is the tray assembly 34 of the system 10 (see FIGS. 5A and 5B). The tray assembly 34 and the hand warmers 40 provide a portable incubation device. The containment device 12 may be incubated for a suitable amount of time at a suitable temperature to augment the production of thrombin within the autologous blood fluid F. The containment device 12 may be incubated at room temperature for approximately one additional minute to ensure all reactions are complete.

Figure 9:
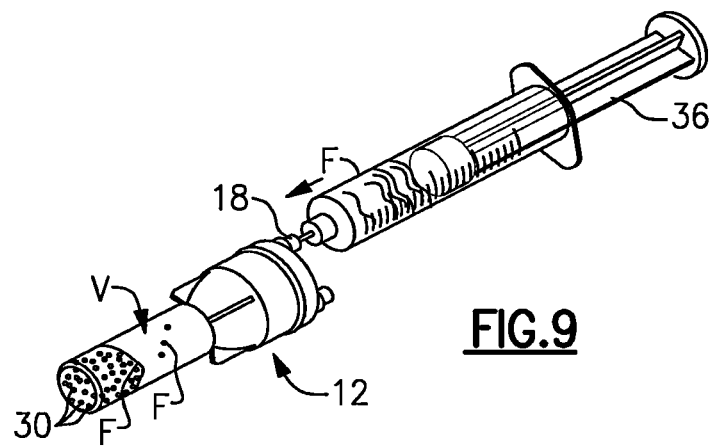
FIG. 9 schematically illustrates adding additional autologous blood fluid to the containment device.
Figure 10:
FIG. 10 schematically illustrates additional steps for preparing a thrombin serum within the containment device.

An additional amount of the autologous blood fluid F is next added to the containment device 12 as shown in FIG. 9. The containment device 12 may then be shaken vigorously for approximately ten seconds and then incubated a second time for approximately one minute (see FIG. 10). These amounts of time are considered exemplary and are not intended to limit this disclosure. The procedure of shaking and incubating may be repeated to ensure that a clot forms in the autologous blood fluid F. The containment device 12 is then gently tapped to break the clot that has formed inside (schematically shown in FIG. 10).

Figure 11:
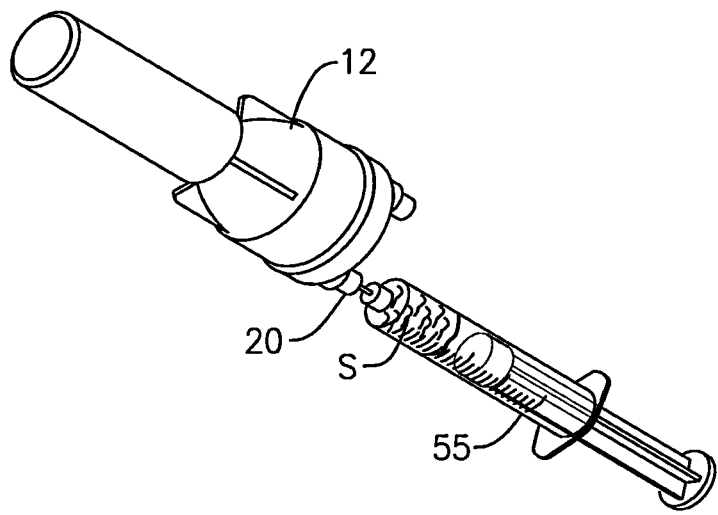
FIG. 11 schematically illustrates withdrawing a thrombin serum from the containment device.

FIG. 11 illustrates removal of a thrombin serum S from the containment device 12. The thrombin serum S can be extracted through the outlet port 20 of the containment device 12 by attaching another syringe 55 to the outlet port 20 and actuating a plunger of the syringe 55.

Figure 12A:
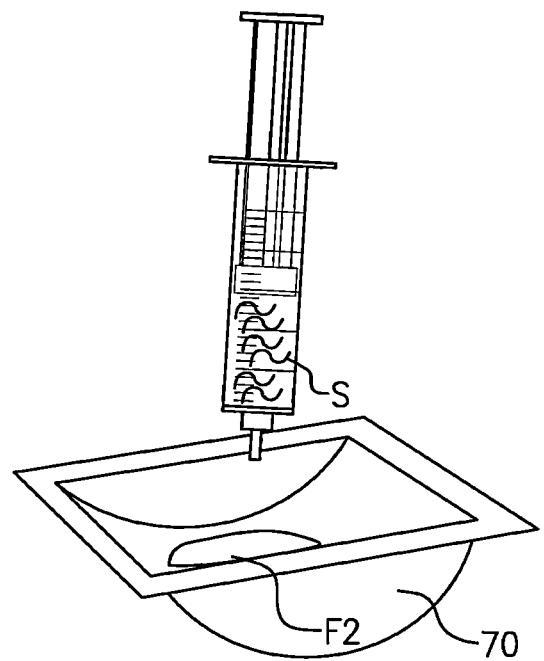
FIGS. 12A and 12B schematically illustrate adding a thrombin serum to a second autologous blood fluid to produce a clot.
Figure 12B:
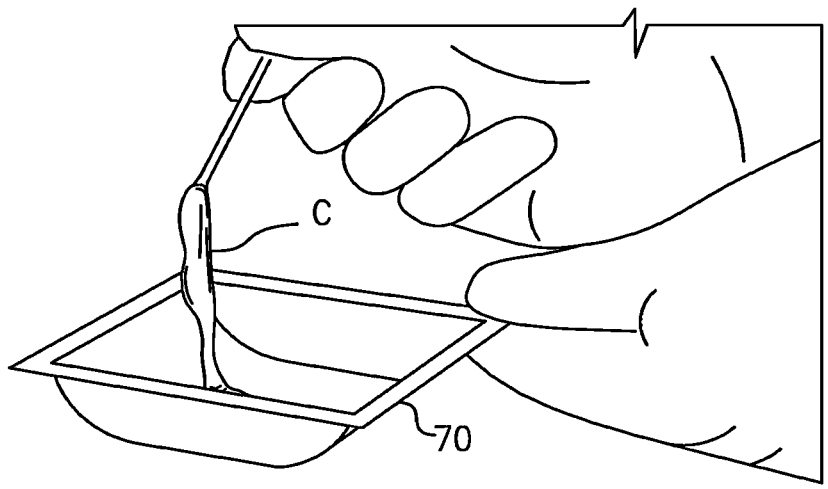
Figure 13A:
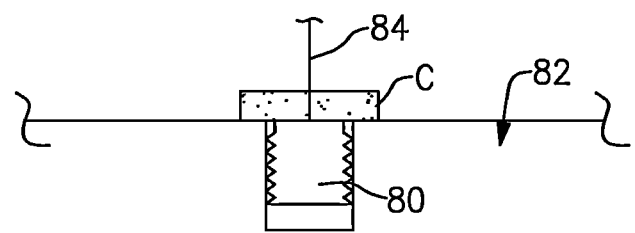
FIGS. 13A and 13B schematically illustrate exemplary surgical uses of a clotted product that is produced by adding a thrombin serum to an autologous blood fluid.
Figure 13B:
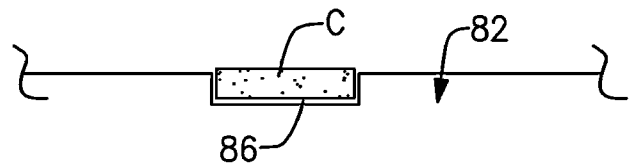

Referring now to FIGS. 12A and 12B, the thrombin serum S may be mixed with a second autologous blood fluid F2 in a dish 70. The second autologous blood fluid F2 may be the same or a different type of fluid as/from the autologous blood fluid F originally added to the containment device 12. In a non-limiting embodiment, the second autologous blood fluid F2 is a non-anti-coagulated autologous blood fluid. The second autologous blood fluid F2 could include whole blood, PRP, PPP, or any combinations of these fluids.

In another non-limiting embodiment, three parts of the second autologous blood fluid F are mixed with one part of the thrombin serum S within the dish (see FIG. 12A). Other ratios are also contemplated, including but not limited to rations of 1:1, 1:3, 1:4, 1:10, 1:11, etc. After a relatively short period of time, the mixture of the second autologous blood fluid F2 and the thrombin serum S produces a clotted product C (see FIG. 12B). The clotted product C may then be removed from the dish 70.

The clotted product C has many potential surgical uses. In a first non-limiting embodiment, shown in FIG. 13A, the clotted product C can placed over top of an implant 80 that has been inserted into tissue 82 (e.g., soft or hard tissue including bone) to augment a tissue repair. The clotted product C could optionally be threaded onto a suture 84 to aid in its placement. In another non-limiting embodiment, shown in FIG. 13B, the clotted product C can be used to repair or plug a void 86 in tissue 82. Other exemplary surgical uses include using the clotted product C to treat a wound or to control bleeding.

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments. Indeed, the embodiments, examples and alternatives of the preceding paragraphs, the claims, or the following description and drawings, including any of their various aspects or respective individual features, may be practiced independently or in any combination. Features described in connection with one embodiment are applicable to all embodiments, unless such features are incompatible.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

The invention claimed is:

1. A method for preparing a clotted blood product, comprising:
   incubating a first autologous blood fluid in a containment device, wherein the containment device comprises:
   (a) a longitudinal axis;
   (b) a cage received within said containment device, the cage having a wall or walls that extend along a longitudinal axis into the containment device, wherein the cage wall or walls include a plurality of openings;
   (c) a cap attached to said containment device;
   (d) an inlet port configured to introduce the first autologous blood fluid into said containment device, wherein the inlet port is located radially outwardly of the cage relative to the longitudinal axis, such that a fluid is delivered to the containment device between an inner wall of the containment device and an outer wall of the cage; and
   (e) an outlet port configured to remove a thrombin serum from said containment device;
   extracting a thrombin serum from the containment device;
   adding the thrombin serum to a second autologous blood fluid to produce a clotted product; and
   collecting the clotted product.

2. The method of claim 1, wherein the clotted product is placed over the top of an implant in a patient.

3. The method of claim 1, wherein the clotted product is threaded onto a suture.

4. The method of claim 1, wherein the clotted product is placed into a void in a tissue of a patient.

5. The method of claim 1, wherein the first autologous blood fluid is a non-anticoagulated autologous blood fluid.

6. The method of claim 1, wherein the second autologous blood fluid is a non-anticoagulated autologous blood fluid.

7. The method of claim 1, wherein the first autologous blood fluid is whole blood, platelet rich plasma, platelet poor plasma, or a combination thereof.

8. The method of claim 1, wherein the second autologous blood fluid is whole blood, platelet rich plasma, platelet poor plasma, or a combination thereof.

9. The method of claim 1, comprising, prior to extracting the thrombin serum,
   adding an additional amount of the first autologous blood fluid to the containment device;
   shaking or inverting the containment device; and
   incubating the containment device a second time.

10. The method of claim 9, further comprising shaking or inverting the containment device a second time, and incubating the containment device a third time.

11. The method of claim 1, comprising, prior to adding the first autologous blood fluid, adding a plurality of beads to the containment device.

12. The method of claim 11, wherein the plurality of beads are borosilicate beads, metal beads, or plastic beads.

13. The method of claim 11, comprising a hydrophilic or hydrophobic surface coating on at least one of the plurality of beads, the cage, or an inner surface of the containment device.

14. The method of claim 1, wherein the second autologous blood fluid is a different type of fluid than the first autologous blood fluid.

15. The method of claim 1, wherein the outlet port comprises a filter attached to either the outlet port or to an opening that receives the outlet port.

* * * * *